United States Patent
Yeo et al.

(10) Patent No.: US 7,572,229 B2
(45) Date of Patent: Aug. 11, 2009

(54) PROBE FOR USE IN MEASURING A BIOLOGICAL SIGNAL AND BIOLOGICAL SIGNAL MEASURING SYSTEM INCORPORATING THE PROBE

(75) Inventors: Hyung-sok Yeo, Suwon (KR); Hong-sig Kim, Seongnam (KR); Gil-won Yoon, Seoul (KR)

(73) Assignee: Samsung Electronics Co., Ltd., Suwon, Kyungki-do (KR)

( * ) Notice: Subject to any disclaimer, the term of this patent is extended or adjusted under 35 U.S.C. 154(b) by 518 days.

(21) Appl. No.: 10/632,963

(22) Filed: Aug. 4, 2003

(65) Prior Publication Data

US 2004/0024326 A1 Feb. 5, 2004

(30) Foreign Application Priority Data

Aug. 2, 2002 (KR) ............... 10-2002-0045802

(51) Int. Cl.
*A61B 5/00* (2006.01)
(52) U.S. Cl. .................. 600/500; 600/309; 600/342; 600/485
(58) Field of Classification Search ............... 600/324, 600/335, 344, 310, 300, 301
See application file for complete search history.

(56) References Cited

U.S. PATENT DOCUMENTS

| | | | | |
|---|---|---|---|---|
| 3,810,460 A | * | 5/1974 | Van Nie | .............. 600/479 |
| 4,017,028 A | * | 4/1977 | Manor | .............. 126/592 |
| 4,580,574 A | * | 4/1986 | Gavish | .............. 600/449 |
| 4,883,353 A | * | 11/1989 | Hausman et al. | .............. 356/41 |
| 4,915,116 A | | 4/1990 | Hasebe et al. | |
| 4,971,062 A | | 11/1990 | Hasebe et al. | .............. 128/664 |
| 5,427,093 A | * | 6/1995 | Ogawa et al. | .............. 600/323 |
| 5,827,181 A | | 10/1998 | Dias et al. | |
| 6,064,898 A | | 5/2000 | Aldrich | .............. 600/316 |
| 6,154,667 A | * | 11/2000 | Miura et al. | .............. 600/323 |
| 6,253,097 B1 | * | 6/2001 | Aronow et al. | .............. 600/310 |
| 6,606,509 B2 | * | 8/2003 | Schmitt | .............. 600/310 |

FOREIGN PATENT DOCUMENTS

| | | |
|---|---|---|
| CN | 1228014 | 9/1999 |
| WO | WO 94/23643 A1 | 10/1994 |
| WO | WO 98/04182 A2 | 2/1998 |
| WO | WO 98/04182 A3 | 2/1998 |
| WO | WO 01/67946 A1 | 9/2001 |

\* cited by examiner

*Primary Examiner*—Robert L Nasser
(74) *Attorney, Agent, or Firm*—Lee & Morse, P.C.

(57) ABSTRACT

A probe for use in photoplethysmographic (PPG) measurement includes a light source unit including a light source that contacts a predetermined site of an object and emits light onto the predetermined site, a photodetector unit positioned facing the light source unit to receive the light emitted from the light source unit and transmitted through the object, a body having a space for receiving the object and in which the light source unit and the photodetector unit are positioned in a same optical axis, and a pressure application unit coupled to the body for applying a pressure to the object via the light source unit. A biological signal measuring system includes the above probe, a controller for controlling operations of the probe and for recording and analyzing signals output from the probe, a detected light intensity display unit for displaying an intensity of detected light, and a biological signal display unit.

25 Claims, 8 Drawing Sheets

PROBE FOR USE IN MEASURING A BIOLOGICAL SIGNAL AND BIOLOGICAL SIGNAL MEASURING SYSTEM INCORPORATING THE PROBE

BACKGROUND OF THE INVENTION

1. Field of the Invention

The present invention relates to a probe for use in measuring a biological signal and a biological signal measuring system incorporating the probe.

2. Description of the Related Art

Pulsation (i.e., pulse) and blood pressure, like human metabolism, vary among individuals. In addition, blood components, blood volume, and pulsation intensity vary at measuring sites of a subject, and even at the same measuring site depending on when the measurement is performed and the subject's physical state. Accordingly, reliable biological signal measuring devices with the ability to provide accurate biological information on a subject are required. Such a measuring device may be a probe that provides information, such as a photoplethysmogram.

Biological signal measurement sites should not cause stress to a patient subjected to a biological signal measurement, but should allow measurement of a faint biological signal from a patient's body. For these reasons, biological signals are commonly measured at a patient's finger.

Pulsation is the most commonly measured biological signal. The elasticity of blood vessels that reach a fingertip, blood circulation status, and weakness of blood vessels all can be measured from a fingertip pulsation measurement. In addition, arterial and peripheral blood vessel disorders can be diagnosed at an earlier stage.

Methods of measuring pulsation, which indicate the beating status of the heart, blood vessel status, and blood circulation status, can be classified into blood pressure measurement and photoplethysmography. Blood pressure measurement refers to the measurement of a change in blood pressure in a blood vessel using a noninvasive sensor. Photoplethysmography refers to the-measurement of blood volume change in a peripheral blood vessel, using an intensity of a light transmitted through a predetermined site on the subject's body.

Conventionally, a photoplethysmogram of a subject can be measured at the subject's finger using a probe. However, it may not be known whether the subject's fingernail accurately contacts a light source of the conventional probe. More specifically, light may radiate onto a skin site, not a fingernail and noise may be incorporated into a resulting photoplethysmogram. Although the fingernail may contact the light source, noise components from external light or external circumstances may be generated if the contact pressure between the fingernail and the light source is insufficient, i.e., not within a proper range, thus leading to unreliable diagnosis results.

SUMMARY OF THE INVENTION

The present invention provides a probe for use in measuring a biological signal that minimizes the generation of noise caused from external light and/or noise caused from the movement of a subject in a measured biological signal such as a photoplethysmographic (PPG) wave, and raises a biological signal-to-noise ratio to ensure more reliable measurement results. The present invention also provides a biological signal measuring system incorporating the above probe.

In accordance with an aspect of the present invention, there is provided a probe for use in photoplethysmographic (PPG) measurement including a light source unit including a light source that contacts a predetermined site of an object and emits light onto the predetermined site, a photodetector unit positioned facing the light source unit to receive the light emitted from the light source unit and transmitted through the object, a body having a space for receiving the object and in which the light source unit and the photodetector unit are positioned in a same optical axis, and a pressure application unit coupled to the body for applying a pressure to the object via the light source unit. The light source unit may include a light emitting diode as a light source. The photodetector unit may include a photoelectric converter for converting light detected by the photodetector unit into an electric signal.

In an embodiment of the present invention, the pressure application unit may be aligned in the same optical axis as the light source unit and the photodetector unit. The pressure application unit may include a nut attached to an upper surface of the light source unit to be movable in a vertical direction and a bolt coupled to the nut. The probe may further include a heat dissipating plate between the nut and the light source unit. The probe may further include an elastic member between the nut and the light source unit. The probe may further comprise a heat dissipating plate between the elastic member and the light source unit.

Alternately, the pressure application unit may include a structure having a horizontal portion and a vertical portion, wherein the horizontal portion contacts an upper surface of the body when the body is void of the object and protrudes above the upper surface of the body when the object is inserted into the body, and wherein the vertical portion of the structure is connected in a perpendicular direction to the horizontal portion of the structure and has an end connected to the light source through a through hole in an upper horizontal portion of the body, and an elastic member surrounding the vertical portion of the structure between the body and the light source unit such that an elastic force is exerted on the body and the light source unit.

Alternately, the pressure application unit may include a structure having a weight sufficient to apply pressure to the object, and a horizontal portion and a vertical portion, wherein the vertical portion of the structure is connected in a perpendicular direction to the horizontal portion of the structure and has an end connected to the light source unit through a through hole in an upper horizontal portion of the body.

The probe may further include a pressure application break button electrically connected to the probe for allowing the subject or an operator to cease the application of pressure by the pressure application unit.

In accordance with another aspect of the present invention, there is provided a biological signal measuring system including a probe in which light is emitted onto a predetermined site of an object and the light transmitted through the object is detected, a controller for controlling the operation of the probe and for recording and analyzing signals output from the probe, a detected light intensity display unit for displaying an intensity of light detected by the probe, and a biological signal display unit connected to the detected light intensity display unit for displaying a biological signal measured from an object, wherein the probe includes: a light source unit including a light source that contacts a predetermined site of the object and emits light onto the predetermined site, a photodetector unit positioned facing the light source unit for receiving the light emitted from the light source unit and transmitted through the object, a body having a space for receiving the object and in which the light source unit and the photodetector unit are positioned in a same optical axis, and a pressure application unit coupled to the body for applying pressure to the object via the light source unit.

The biological signal display unit may be a photoplethysmographic (PPG) display unit that displays a photoplethysmographic (PPG) wave from the object. The controller is preferably a microprocessor. The system may further include an analog-to-digital converter (ADC), a programmable logic device (PLD), or a processor for recording a measured PPG wave.

When using the probe and the biological signal measuring system according to the present invention described above, it is possible to minimize the generation of noise arising from the movement of a subject and from external factors, such as external light, during the measurement of a PPG wave. Accordingly, the measured PPG wave has an increased signal-to-noise ratio and is more reliable.

BRIEF DESCRIPTION OF THE DRAWINGS

The above and other aspects, features and advantages of the present invention will become more apparent to those of ordinary skill in the art by describing in detail exemplary embodiments thereof with reference to the attached drawings in which.

DETAILED DESCRIPTION OF THE INVENTION

Figure 1:
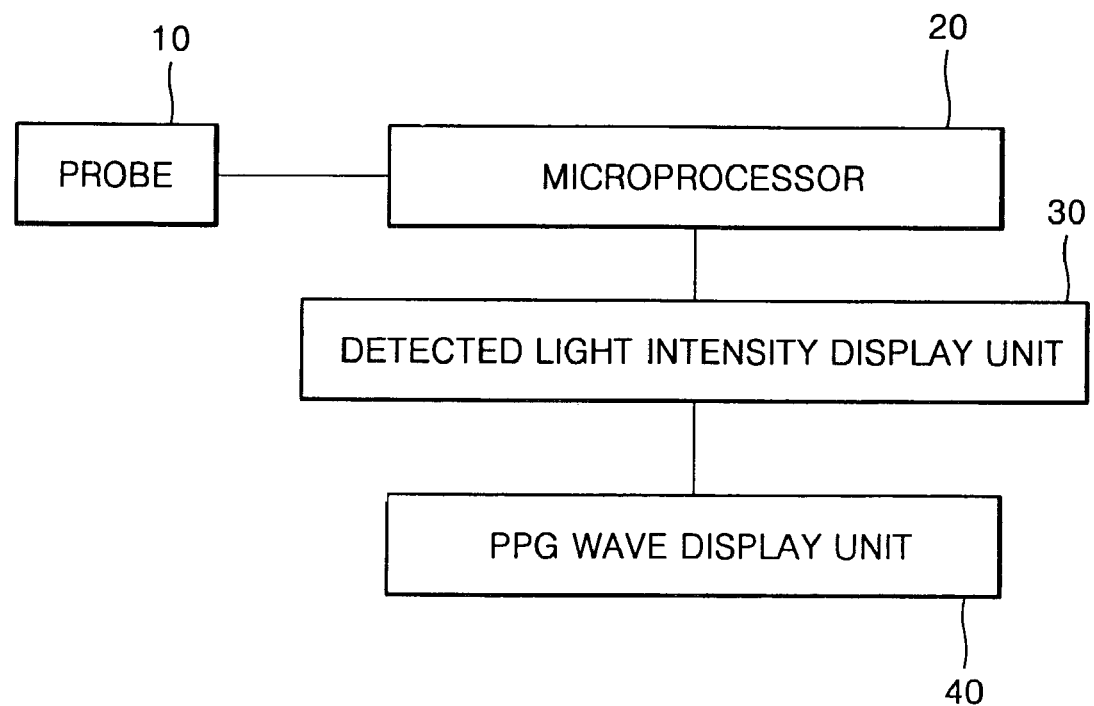
FIG. 1 is a box diagram of a photoplethysmographic (PPG) measuring system according to an embodiment of the present invention.

Korean Patent Application No. 2002-45802, filed on Aug. 2, 2002, and entitled: "Probe for Use in Measuring Biological Signal and Biological Signal Measuring System with the Probe," is hereby incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout.

In order to achieve an accurate analysis of the physiological status or blood components of a subject, a measurement of a subject's biological signal, such as a photoplethysmographic (PPG) wave, having a high signal-to-noise ratio must take precedence over other factors. For example, photoplethysmography requires a minimization of noise (hereinafter, motion noise) caused by the movement of a subject and noise (hereinafter, external noise) caused by various environmental factors, such as external light. In addition, individual variations need to be taken into account.

In a probe according to the present invention, a distance between a light source, which emits measurement light, and a photodetector, which detects the light emitted from the light source and transmitted through an object, is adjusted to minimize motion noise, external noise, and individual variations, such as the thickness or stiffness of the object. The probe according to the present invention will be described in detail below. Although a biological signal detected with the probe is described as being a PPG wave in the following description, other biological signals may be detected with the probe according to the present invention without limitation.

Referring to FIG. 1, a PPG measuring system according to an embodiment of the present invention includes a probe 10 having a pressure application unit, a light source unit, and a photodetector unit. In operation, the pressure application unit applies a predetermined amount of pressure to an object inserted into the probe, the light source unit emits light for a PPG measurement, and the photodetector unit, which is arranged facing the light source unit, detects light transmitted through the object. The PPG measuring system further includes a microprocessor 20, a detected light intensity display unit 30, and a PPG wave display unit 40. The microprocessor 20 controls the operation of the probe 10 and records and analyzes signals output from the probe 10. The detected light intensity display unit 30 is connected to the probe 10 via the microprocessor 20 and displays a graph of voltage proportional to the intensity of light received by the photodetector unit of the probe 10 under the control of the microprocessor 20. The PPG wave display unit 40 is connected to the detected light intensity display unit 30 and displays a photoplethysmogram measured by the probe 10 under the control of the microprocessor 20.

Voltage proportional to the intensity of light transmitted through a measurement site and detected by the photodetector unit, hereinafter referred to as transmission light intensity (i.e., detected light intensity) is displayed on the detected light intensity display unit 30 and distinguished from the intensity of light (i.e., emission light intensity) just emitted from the light source unit. The transmission light intensity offers information on the tissue of the object present in the path of the light, for example, information on a diameter of a blood vessel in the tissue and a blood volume and blood components thereof. Changes in the tissue of the object, such as blood vessel diameter change and volume change, are affected by change of pressure inside the blood vessel. A PPG wave of the object can be read by measuring these changes in the object. As such, information on the change in the object's tissue is closely related with information on the PPG wave of the object. In particular, a change in the object's tissue leads to a change in an absorbance of light thereof, such as near infrared light, and a change in the transmission light intensity. The change in the transmission light intensity offers information on the PPG wave of the object. The PPG wave displayed on the PPG display unit 40 is obtained through an analysis of the transmission light intensity.

FIGS. 2 through 8 illustrate various embodiments of the probe 10 as shown in FIG. 1.

Figure 2:
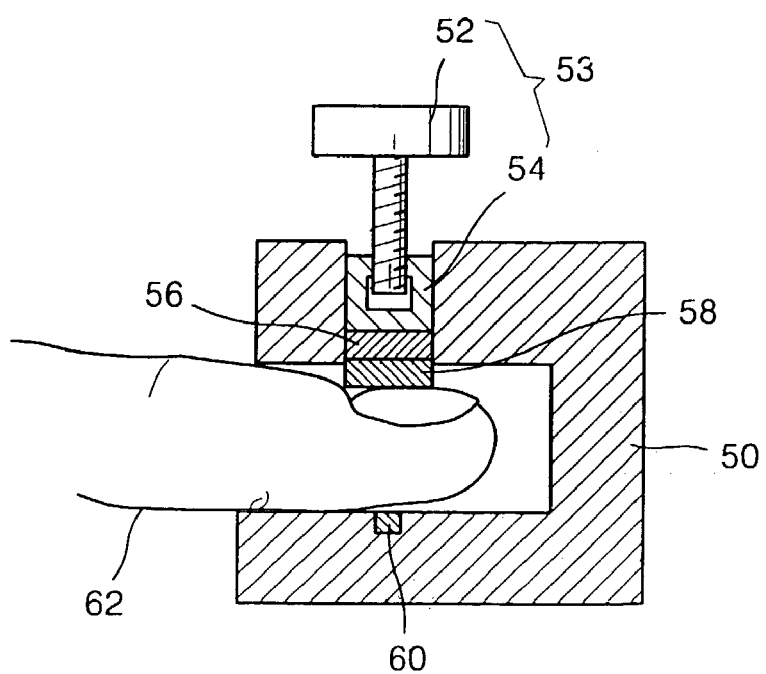
FIG. 2 illustrates a sectional view of a first embodiment of a probe as shown in FIG. 1.

Referring to FIG. 2, a first embodiment of the probe 10 includes a body 50 having a space into which an object 62, for example, a finger, is inserted, a light source unit 58, and a photodetector unit 60. The body 50 consists of parallel upper and lower portions and a vertical portion connecting the upper and lower portions. The light source unit 58, which includes a light source, such as a light emitting diode (LED), for emitting measurement light near the cuticle of the finger, is positioned at a predetermined location on the upper horizontal portion of the body 50. The light source unit 58 may protrude from the upper horizontal portion of the body toward the photodetector unit 60. It is preferable that the light source unit 58 protrudes to such a degree that a subject becomes aware that his/her fingernail has contacted the light source unit 58 when the object 62, i.e., the finger, is inserted into the probe 10. i.e., between the upper and lower horizontal portions of the body 50. The photodetector unit 60 is positioned at a predetermined location on the lower horizontal portion of the body 50 facing the light source unit 58. The photodetector unit 60 detects light emitted from the light source unit 58 and transmitted through the object 62. The photodetector unit 60 includes a photoelectrical converter which converts the light detected by the photodetector unit 60 into an electrical signal. It is preferable that the photodetector unit 60 and the light source unit 58 are arranged in the same optical axis, i.e., they are coaxially arranged. For example, the photodetector unit 60 and the light source unit 58 may be arranged on a vertical axis, i.e., with respect to the upper and lower horizontal portions of the body 50.

In order to detect a PPG wave containing minimal motion noise and external noise, it is preferable to minimize a distance between the light source unit 58 and the photodetector unit 60 so that the photodetector unit 60 is able to detect a PPG wave having a maximum alternating current (AC) amplitude. To this end, a predetermined amount of pressure, which is insufficient to cause the subject to experience any pain, may be applied to the fingernail of the subject after the fingernail has contacted the protruding light source unit 58. e.g., the light source, to reduce the distance between the light source unit 58 and the photodetector unit 60. For this purpose, a pressure-application unit 53 for applying a predetermined amount of pressure to a given portion of the object 62, via the light source unit 58, is positioned above the light source unit 58. In addition, a heat dissipating plate 56, which externally dissipates heat generated by the light source unit 58, is positioned between the pressure application unit 53 and the light source unit 58.

The pressure application unit 53 includes a bolt 52 and a nut 54. The bolt 52 and the nut 54 are screw coupled. When the bolt 52 is turned, the nut 54 moves downwardly in a vertical direction, preferably, along the optical axis that optically connects a center of the light source unit 58 and a center of the photodetector unit 60. Alternatively, the bolt 52 and the nut 54 may be formed as an integrated single body that moves vertically along the optical axis. In this case, when the bolt 52 and the nut 54, which are combined together, are turned in the same direction, the nut 54 engages a threaded portion (not shown) formed on an inner wall of the body 50. The pressure application unit 53 may be pushed manually by the subject or may be engaged automatically when the object 62 reaches a given position in the probe.

When the pressure application unit 53 operates automatically, it is preferable to determine whether to continue the application of pressure based on variations in the intensity of detected light and the distance between the light source unit 58 and the photodetector unit 60 with respect to the applied pressure. Since the object 62 is elastically compressible, the distance between the light source unit 58 and the photodetector unit 60 decreases rapidly at first and gradually slows until full compression is achieved. It is preferable to stop the operation of the pressure application unit 53 and measure a PPG wave when the distance between the light source unit 58 and the photodetector unit 60 becomes constant. The operation of the pressure application unit 53, however, may be stopped to measure a PPG wave when the transmission light intensity displayed on the detected light intensity display unit 30 is optimal, even before the distance between the light source unit 58 and the photodetector unit 60 becomes constant. When the pressure application unit 53 is designed to automatically operate, the probe may further include a pressure sensor (not shown) for sensing the amount of pressure applied from the pressure application unit 53 to the object 62 as controlled by the microprocessor 20, i.e., a sensor capable of sensing a variation in the distance between the light source unit 58 and the photodetector unit 60. After measurement, the measured PPG wave is recorded using an analog-to-digital converter (ADC), a programmable logic device (PLD), or a processor.

When the pressure application unit 53 is designed to operate automatically as described above, a significant design consideration is to avoid hurting the subject during compression. To this end, it is preferable to operate the pressure application unit 53 slowly to allow the subject to promptly respond if pain is experienced during compression. In addition, it is preferable that the PPG measuring system is configured to be able to stop the operation of the pressure application unit 53 immediately when the subject experiences pain at the measurement site during the application of pressure. In general, pressure levels applied from the pressure application unit 53 and corresponding pain sensations are stored in a database to allow the microprocessor 20, which is a system controller, to automatically stop the operation of the pressure application unit 53.

For sensitive subjects, it is preferable that the PPG measuring system further includes a device that enables the subject or a system operator to quickly stop compression of the subject's measurement site. Such a device may include a first pressure application break button, attached to the probe of FIG. 2, to allow the subject to push it as necessary and/or a second pressure application break button formed in a system manipulation panel to allow the system operator to push it as necessary. When either the first or second pressure application break button is pushed, the PPG measuring system processes a signal generated by the pushing of the first or second pressure application break button with priority over other signals.

For comparison, the above descriptions of the first embodiment of the pressure application unit 53 may be referred to when other embodiments of the pressure application unit 53 are subsequently described.

Various pressure application units may be applicable. FIGS. 3 through 8 illustrate other probes having various embodiments of pressure application units.

Figure 3:
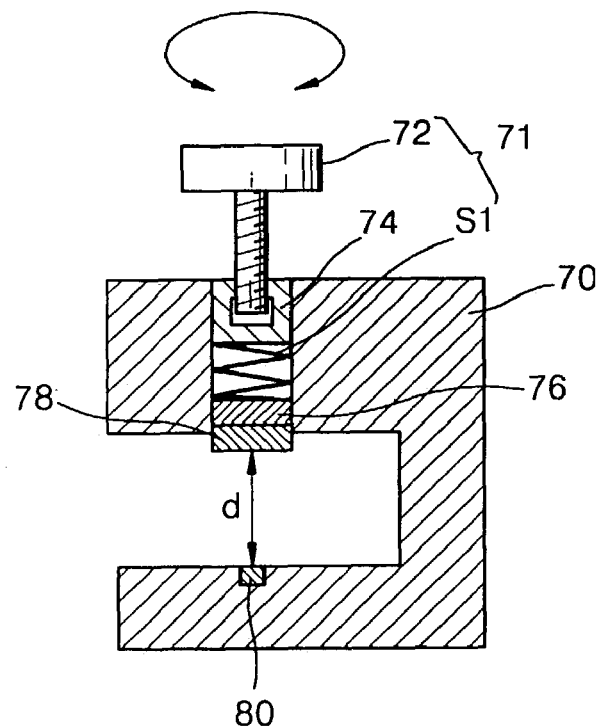
FIG. 3 illustrates a sectional view of a second embodiment of a probe as shown in FIG. 1.
Figure 4:
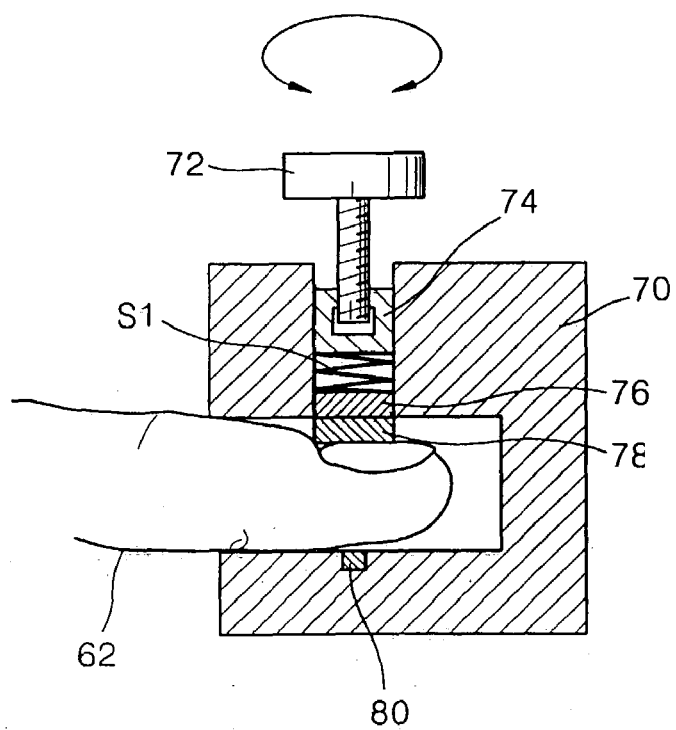
FIG. 4 illustrates a sectional view of the probe of FIG. 3 when a subject's finger is inserted thereinto.

The probe shown in FIG. 3 includes a photodetector unit 80 in a lower horizontal portion of a body 70 and a second embodiment of a pressure application unit 71 in an upper horizontal portion of the body 70 opposite to the photodetector unit 80. The second embodiment of the pressure application unit 71 includes a bolt 72, a nut 74, and an elastic member S1. The bolt 72 and the nut 74 are similar to the bolt 52 and the nut 54 in the first embodiment of the pressure application unit 53, as shown in FIG. 2. The elastic member S1 is implemented with a spring between the nut 74 and the light source unit 78. The elastic member S1 offers a buffering function when pressure is applied via the light source unit 78 to a given site of the object 62, for example, to the flesh near the fingernail, after the object 62 is inserted into the body 70, as shown in FIG. 4. A heat dissipating plate 76 is positioned between the elastic member S1 and the light source unit 78. The light source unit 78 includes a light source, for example, a LED, positioned below the pressure application unit 71 that protrudes from the upper horizontal portion of the body toward the photodetector unit 80. The light source unit 78 and the heat dissipating plate 76 are similar to the light source unit 58 and the heat dissipating unit 56, respectively, of FIG. 2. In FIG. 3, reference character "d" denotes a distance between the protruding light source and the photodetector unit 80.

Figure 5:
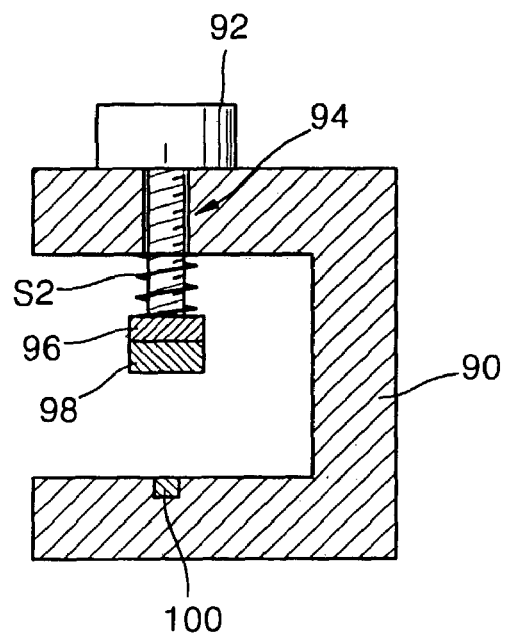
FIG. 5 illustrates a sectional view of a third embodiment of a probe as shown in FIG. 1.
Figure 6:
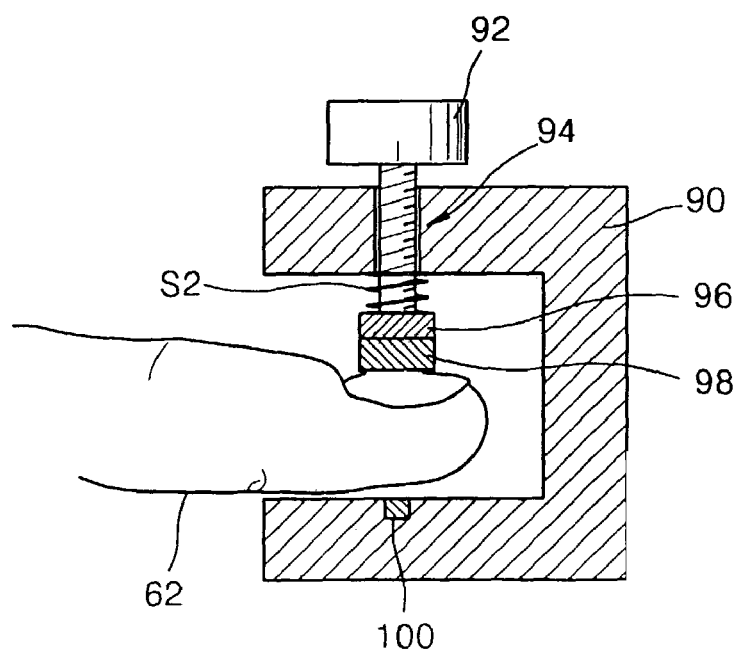
FIG. 6 illustrates a sectional view of the probe of FIG. 5 when a subject's finger is inserted thereinto.

The probe shown in FIGS. 5 and 6 includes a third embodiment of a pressure application unit that contacts a top surface of a heat dissipating plate 96 having a bottom surface contacting a light source unit 98. It is preferable that the third embodiment of the pressure application unit is coaxial with the light source unit 98 and a photodetector unit 100. The pressure application unit according to the third embodiment of the present invention includes a structure 92 having a horizontal portion positioned parallel to the upper horizontal portion of a body 90 and a vertical portion extending downward through the upper horizontal portion of the body 90. A first end of the vertically extending downward portion of the structure 92 is connected to the top surface of the heat dissipating plate 96 and a second end, opposite to the first end, is connected to the horizontal portion of the structure 92. An elastic member S2 surrounds a portion of the vertical portion of the structure 92 protruding out from a bottom of the upper horizontal portion of the body 90 and is positioned between the bottom of the upper horizontal portion of the body 90 and the heat dissipating plate 96.

A through hole 94, through which the vertical portion of the structure 92 is-inserted, is formed in the upper horizontal portion of the body 90. The elastic member S2 is a spring having an inner diameter that is at least equal to the diameter of the through hole 94. An upper end of the elastic member S2 contacts the edge of the through hole 94 at the bottom of the upper horizontal portion of the body 90 and a lower end thereof contacts the top surface of the heat dissipating plate 96, such that the elastic force of the elastic member S2 is exerted on the upper horizontal portion of the body 90 and the heat dissipating plate 96. The horizontal portion of the structure 92 is moved toward the photodetector unit 100 by the elastic force of the elastic member S2 to tightly contact the top surface of the upper horizontal portion of the body 90. The light source unit 98 attached to the bottom surface of the heat dissipating plate 96 is moved away from the upper horizontal portion of the body 90 toward the photodetector unit 100. As described above, the structure 92 is kept in contact with the upper horizontal portion of the body 90 by the elastic member S2 before the object 62 is inserted into the body 90 of the probe.

When the object 62 is inserted into the body 90 of the probe, as shown in FIG. 6, the flesh around the fingernail of the object 62 contacts the light source of the light source unit 98 and pushes it upward away from the photodetector unit 100. As a result, the elastic member S2 is compressed, and the upper end of the vertical portion of the structure 92 protrudes above the upper horizontal portion of the body 90. The elastic force of the elastic member S2 is exerted on the object 62 placed in the optical axis of the light source unit 98 and the photodetector unit 100, so that the object 62 is compressed. The elastic force of the elastic member S2 ensures that the object 62 tightly contacts both the light source of the light source unit 98 and the photodetector unit 100, thereby decreasing generation of motion noise and external noise.

Although a compression force of the elastic member S2 is used in the probe of FIGS. 5 and 6, a tensile force of the elastic member S2 may be applied to compress the object, for example, by externally connecting a spring to the structure 92.

Figure 7:
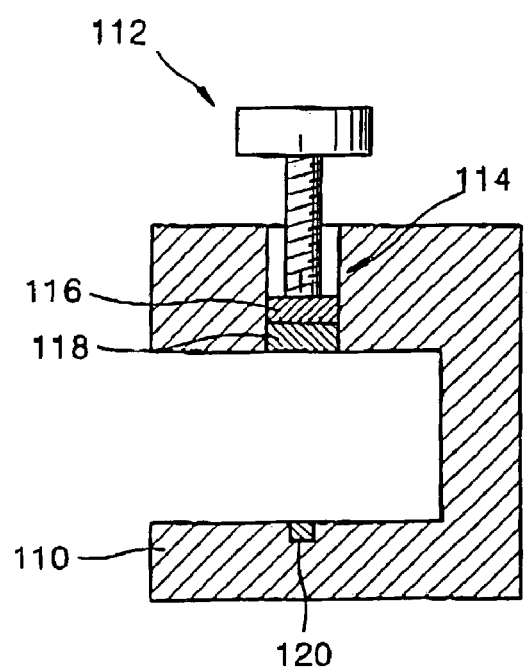
FIG. 7 illustrates a sectional view of a fourth embodiment of a probe as shown in FIG. 1.
Figure 8:
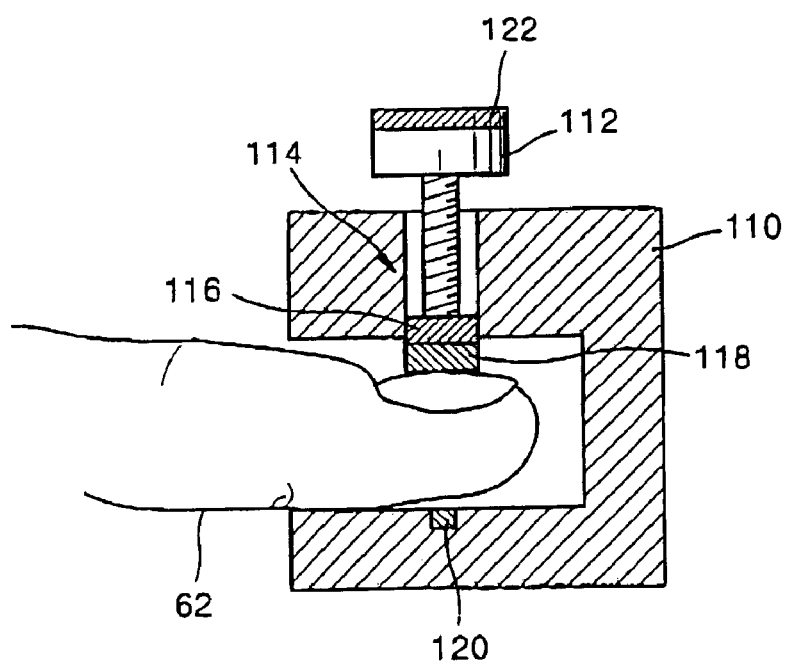
FIG. 8 illustrates a sectional view of the probe of FIG. 7 when a subject's finger is inserted thereinto.

FIGS. 7 and 8 illustrate a probe with a fourth embodiment of a pressure application unit that applies pressure to a measurement site of an object using a weight, before and after an object is inserted into the probe.

Referring to FIGS. 7 and 8, an upper horizontal portion of a body 110 of the probe has a through hole 114 along which a light source unit 118 and a heat dissipating plate 116 are moved up and down. A fourth embodiment of the pressure application unit 112 is connected to the heat dissipating plate 116 via the through hole 114. The fourth embodiment of the pressure application unit 112 is a structure with a vertical portion having a first end connected to the heat dissipating plate 116 and a second end, opposite to the first end, extending vertically out of the through hole 114 above the upper horizontal portion of the body 110, and a horizontal portion connected to the second end of the vertical portion, the horizontal portion being parallel to the upper horizontal portion of the body 110. The fourth embodiment of the pressure application unit 112 is structurally similar to the structure 92 of FIGS. 5 and 6. The horizontal portion of the pressure application unit 112 acts as a stage for a weight element 122 having a predetermined weight. The light source unit 118 does not protrude out from the body 110 toward the photodetector 120, as shown in FIG. 7, before the weight element 122 is placed on the upper horizontal portion of the body 110. However, when the object 62 is inserted to a predetermined location in the body 110 of the probe and the weight element 122 is placed on the horizontal portion of the fourth pressure application unit 112, the light source unit 118 protrudes toward the photodetector unit 120 in proportion to the weight of the weight element 122. If the light source of the light source unit 118 does not reach a measurement site of the object 62, a second, additional weight element (not shown) is placed on the horizontal portion of the pressure application unit 112 to further protrude the light source unit 118 toward the photodetector unit 120. If the pressure applied to the object 62 contacting the light source of the light source unit 118 is insufficient, a third weight element (not shown) may be further placed on the second weight element. It is preferable to select a third weight element having an appropriate weight in consideration of the pressure to be applied to the object 62.

Figure 9:
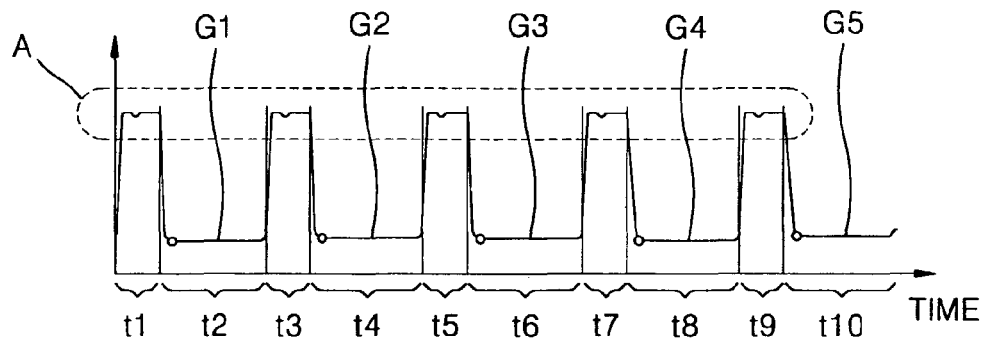
FIGS. 9 through 11 are graphs of voltage proportional to detected light intensity versus time, which are displayed on a detected light intensity display unit of FIG. 1.
Figure 10:
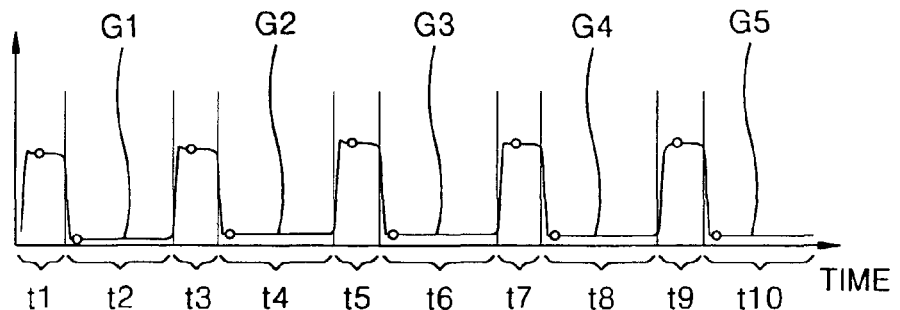
Figure 11:
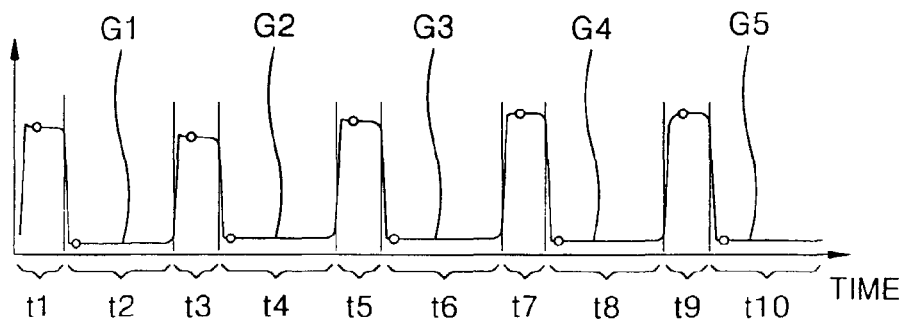

Light intensity detected by the probe and displayed on the detected light intensity display unit 30 of FIG. 1 will now be described with reference to FIGS. 9 through 11. In the following description, it is assumed that the object inserted into the probe is a finger. FIGS. 9 through 11 are graphs of voltage proportional to detected light intensity versus time measured using five different light sources, for example, LEDs, which emit light having different wavelengths.

FIG. 9 is a graph of voltage proportional to detected light intensity versus time before a finger is inserted into the probe. FIG. 10 is a graph of voltage proportional to detected light intensity versus time after the finger is inserted to a given location in the probe but before pressure is applied to the finger. FIG. 11 is a graph of voltage proportional to detected light intensity versus time after pressure is applied to the finger inserted to the given location in the probe.

In FIGS. 9 through 11, times t1, t3, t5, t7, and t9 on the x-axis denote an equal duration of time during which the five light sources are turned on, and times t2, t4, t6, t8, and t10 denote an equal duration of time during which the corresponding five light sources are turned off. Reference characters G1, G2, G3, G4, and G5 denote the emission light intensity from the respective five light sources.

Referring to FIG. 9, before a finger is inserted into the probe, detected light has a saturated AC level, as indicated by region "A." However, when the finger is inserted into the probe and pressure is not applied yet to the finger, the AC level of detected light drops to a baseline having a constant level for all of the wavelengths of light used, as shown in FIG. 10. When pressure is applied to the finger inserted into the probe, as shown in FIG. 11, the AC level rises to a level higher than in the case of FIG. 10. The results support that as a distance between a light source unit and a photodetector unit decreases, the AC level approaches the saturated level of FIG. 9.

Comparing the graphs of FIGS. 10 and 11, it is apparent that when a predetermined amount of pressure is applied to a given site of the finger inserted into the probe and the distance between the light source unit and the photodetector unit is decreased, motion noise caused by the movement of the finger and external noise caused by external factors, such as external light, are reduced. In addition, since the detected light intensity includes information on PPG waves from the finger, the results shown in FIG. 11 also mean that the AC level of the PPG waves is increased so that the detected PPG waves have a higher signal-to-noise ratio.

A process of minimizing a distance between a light source unit and a photodetector unit without causing a subject to experience pain when pressure is applied to a finger inserted into the probe will now be described.

Figure 12:
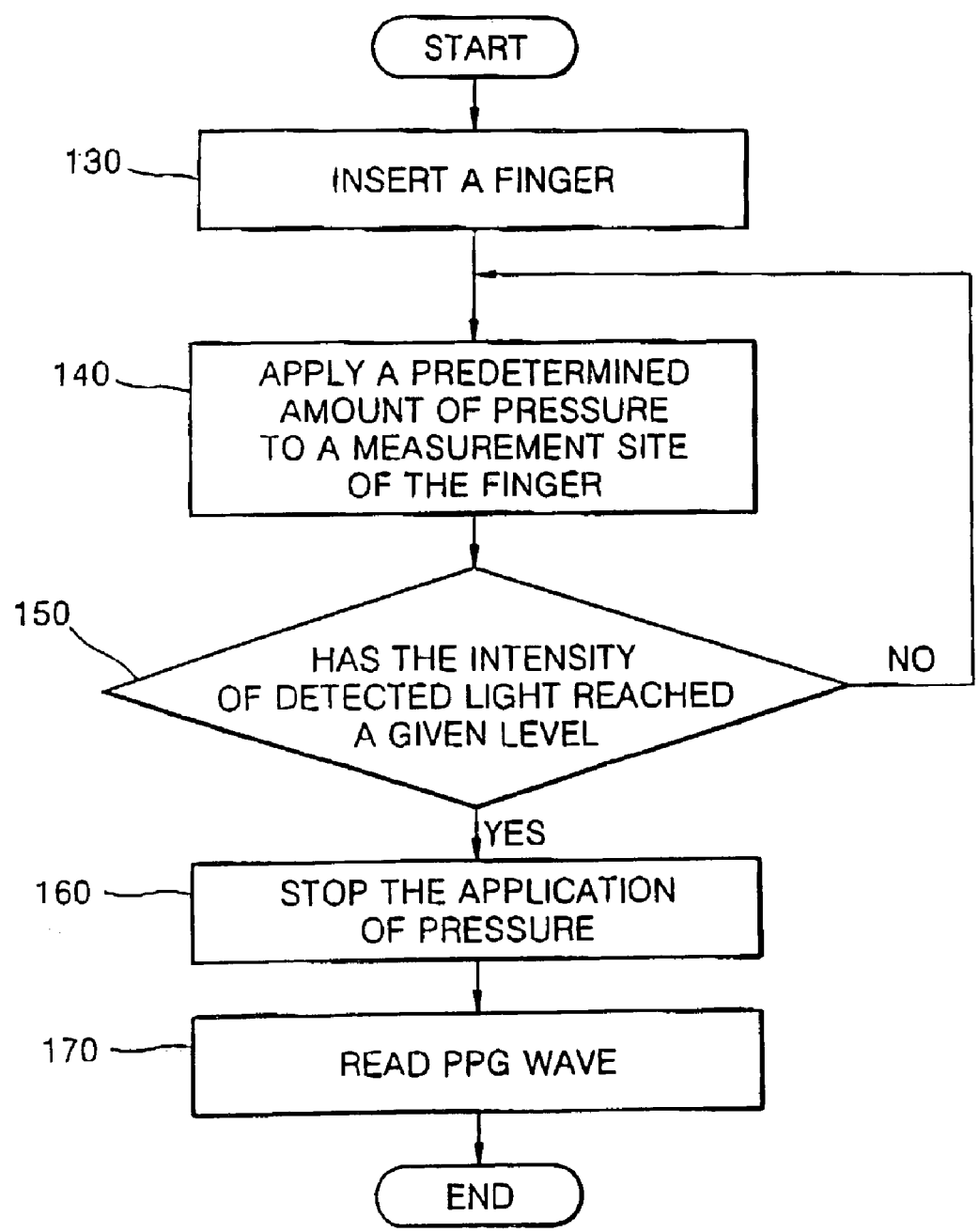
FIG. 12 is a flowchart illustrating a process of reducing the distance between a light source unit and a photodetector unit in the system of FIG. 1 and a process of measuring a PPG-wave therewith.

Referring to FIG. 12, in step 130, a finger is inserted to a predetermined location of the probe. Next, in step 140, a predetermined amount of pressure is slowly applied to a measurement site of the inserted finger using the pressure application unit of the probe. Here, a preferred measurement site of the finger is the flesh around a fingernail. This site is preferable because the least bones and fewest capillary vessels, as compared to other areas of the human body, exist under the flesh around the fingernail. Accordingly, arterial blood can be easily and accurately observed from the flesh around the fingernail. In step 140, it is necessary to apply pressure just to the flesh around the fingernail for more accurate PPG wave measurement.

While pressure is applied to the finger, in step 150, the intensity of detected light as illustrated in FIGS. 9 through 11 is monitored through the detected light intensity display unit to determine whether the intensity of detected light has reached a given level. In step 150, if the intensity of the detected light has reached the given level at which the light source unit is as close as possible to the photodetector unit without hurting the subject, in step 160, the application of pressure to the finger is stopped. In the alternative, if the intensity of the detected light has not yet reached the given level, the application of pressure to the finger is increased provided that the subject has not experienced pain.

As described above, it is preferable to minimize the distance between the light source unit and the photodetector unit in consideration of the status of the subject and the intensity of detected light displayed on the detected light intensity display unit.

If a pressure application break signal, which is generated by a subject activating a signal button and transmitted from the probe, is detected in step 140 or step 150, the pressure application break signal is processed with priority over all other signals. If the application of pressure to the finger is abruptly stopped by the subject, for example, because of an experience of pain, the process returns to the initial step. After the intensity of detected light has reached the given level, in step 160, the application of pressure to the finger is stopped, and, in step 170, the PPG wave is read.

The PPG wave is read through an analysis of the light intensity displayed on the detected light intensity display unit 30 of FIG. 1. The displayed light intensity shows light intensity variations as a result of the interaction between light emitted from the light source unit toward the finger, which is inserted between the light source unit and the photodetector unit, and the internal components of the finger, such as blood vessels and blood. The light intensity includes various types of information on the interaction between the light incident on the finger and the internal components of the finger. The diameter of finger blood vessels and their blood volume vary at a PPG peak and a PPG nadir. Since the PPG wave is periodical, the variation is also periodical. Accordingly, the intensity of light transmitted through the finger also varies periodically depending on the status of the internal components of the finger. Therefore, the PPG wave can be read by analyzing the intensity of detected light.

The PPG wave is read via automated procedures under the control of the microprocessor 20 and displayed on the PPG wave display unit 40.

Figure 13:
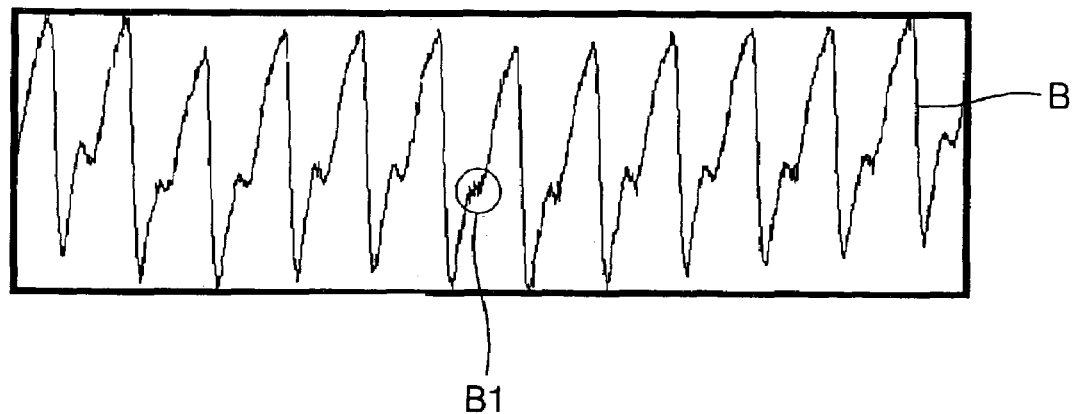
FIGS. 13 through 16 are exemplary photoplenthysmograms measured in various conditions and displayed on a PPG display unit of FIG. 1.
Figure 14:
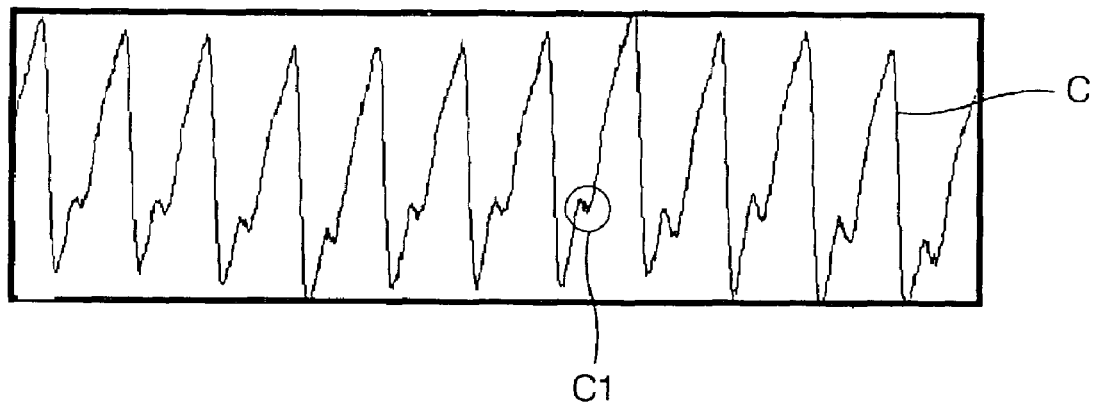

FIGS. 13 through 16 are photoplethysmograms measured under various conditions. In particular, FIG. 13 shows a first PPG wave B measured from a finger inserted into the probe in a state where the light source is kept in place without being moved toward the finger. FIG. 14 shows a second PPG wave C measured in a state where the light source is moved closer to, but not into contact with, the flesh around the fingernail.

Comparing FIGS. 13 and 14, more high frequency noise appears in the first PPG wave B of FIG. 13 than in the second PPG wave C of FIG. 14. In addition, a shoulder C1 of the second PPG wave C is much clearer and sharper than a shoulder B1 of the first PPG wave B.

As is apparent from the comparison between FIGS. 13 and 14, when the light source is extended toward the finger, a greater amplitude PPG wave can be read with greater accuracy, as compared to when the light source is maintained away from the finger.

Figure 15:
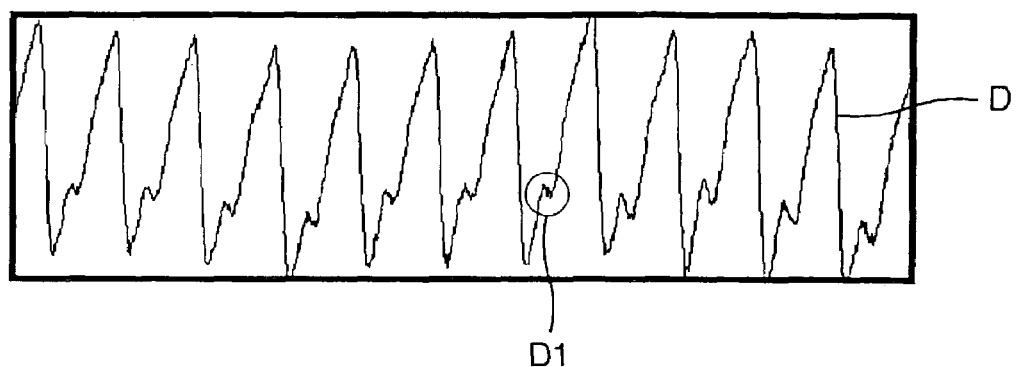
Figure 16:
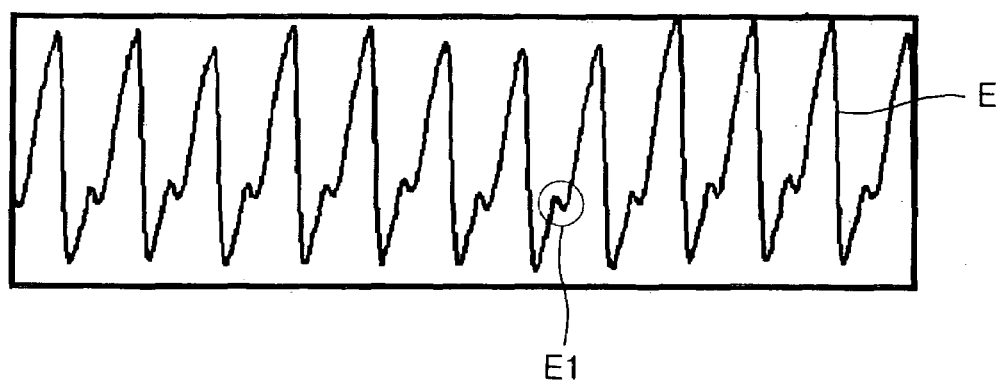

FIG. 15 shows a third PPG wave D measured in a state where the light source is moved to just contact the flesh around the finger inserted into the probe. FIG. 16 shows a fourth PPG wave E measured in a state where a predetermined amount of pressure is applied to the flesh around the finger to further decrease the distance between the light source and the photodetector unit.

Comparing FIGS. 15 and 16, much less high frequency noise appears in the fourth PPG wave E of FIG. 16 than in the third PPG wave D of FIG. 15. In addition, a shoulder E1 of the fourth PPG wave E is much clearer and sharper than a shoulder D1 of the third PPG wave D.

PPG waves vary for each subject depending on the thickness and stiffness of the measurement site, even when a distance between the light source unit and the photodetector unit is constant. Accordingly, it is preferable to consider individual variations when measuring PPG waves as described above. If such individual variations are not considered, noise arising from measurement errors may be generated.

The AC level of detected light includes information on the thickness and stiffness of a measurement object, for example, a finger. Accordingly, individual variations can be read from the AC level proportional to the light intensity displayed on the detected light intensity display unit 30. The AC level of detected light is lower for a thicker and stiffer object than for a thinner and softer object.

Individual variations can be reduced by measuring the initial AC level of light transmitted through the finger in a state where the light source is maintained in an initial position and then by adjusting the amount of pressure applied to the finger to induce a light intensity reduction by as much as a predetermined percentage from the initial AC level. In addition, the predetermined percentage should be adjusted within a range where no pain is experienced and no abnormal arterial blood circulation is caused in the finger by the applied pressure. Resultantly, the range should be different for each subject according to the thickness and stiffness of the measurement site.

As described above, a probe according to the present invention installed in a PPG wave measuring system includes a light source protruding closer to a finger inserted into the probe to allow for accurate light emission onto the flesh around the fingernail irrespective of the finger's size and shape. Accordingly, noise arising from measurement errors can be removed before a PPG wave is measured. In addition, the light source of the probe according to the present invention is pushed to compress a predetermined measurement site of a subject and to be as close as possible to the photodetector unit, thereby minimizing noise caused by the motion of the subject in the resulting PPG wave.

Furthermore, when using a PPG wave measuring system with such a probe according to the present invention, the signal-to-noise ratio of a PPG wave is increased. Accordingly, the PPG wave can be measured with greater accuracy and minimum measurement errors arising from individual variations. A PPG wave with minimum noise can be read more conveniently using a pressure application unit and a detected light intensity display unit. When the probe according to the present invention is applied to a finger type probe equipped with a light source for non-invasive blood component measurement, an ideal PPG wave for blood component analysis can be provided by using the pressure application unit. Optimal pressure levels for varying finger thickness may be stored in a database to accurately analyze blood components for each finger.

The above-described exemplary embodiments of the present invention are for illustrative purposes and are not intended to limit the scope of the invention. Accordingly, it will be understood by those of ordinary skill in the art that although the above probes are designed to apply pressure only to flesh around the fingernail, an alternative probe according to the present invention may have a structure that allows for an application of pressure to both upper and lower portions of a finger inserted into the probe. In addition, an alternative probe according to the present invention may have a cap covering the body of the probe excluding a finger insertion hole to block external noise. An alternative biological signal measuring system according to the present invention may have a single display unit for displaying both the light intensity detected by the photodetector unit and a PPG wave. Accordingly, it will be understood by those of ordinary skill in the art that various changes in form and details may be made without departing from the spirit and scope of the present invention as set forth in the following claims.

What is claimed is:

1. A probe for use in photoplethysmographic (PPG) measurement, comprising:
    a light source unit including a light source, the light source unit adapted to contact a predetermined site of an object and to emit light onto the predetermined site;
    a photodetector unit positioned facing the light source unit to receive the light emitted from the light source unit and transmitted through the object;
    a body having a space for receiving the object and in which the light source unit and the photodetector unit are positioned along a same vertical axis with respect to a surface of the body supporting the object;
    a pressure application unit coupled to the body for applying a pressure to the object via the light source unit, the pressure application unit being aligned in the same vertical axis above the light source unit; and
    a pressure application break button electrically connected to the probe for allowing the subject or an operator to cease the application of pressure by the pressure application unit.

2. The probe as claimed in claim 1 includes:
    a nut attached to an upper surface of the light source unit to be movable in a vertical direction and a bolt coupled to the nut; and
    an elastic member between the nut and the light source unit.

3. The probe as claimed in claim 2, further comprising:
    a heat dissipating plate between the elastic member and the light source unit.

4. The probe as claimed in claim 1, wherein the light source unit comprises a light emitting diode as a light source.

5. The probe as claimed in claim 1, wherein the photodetector unit comprises a photoelectric converter for converting light detected by the photodetector unit into an electric signal.

6. The probe as claimed in claim 2, further comprising:
    a heat dissipating plate between the nut and the light source unit.

7. The probe as claimed in claim 1, wherein the pressure application unit comprises:
    a structure having a horizontal portion and a vertical portion, wherein the horizontal portion contacts an upper surface of the body when the body is void of the object and protrudes above the upper surface of the body when the object is inserted into the body, and wherein the vertical portion of the structure is connected in a perpendicular direction to the horizontal portion of the structure and has an end connected to the light source through a through hole in an upper horizontal portion of the body; and
    an elastic member surrounding the vertical portion of the structure between the body and the light source unit such that an elastic force is exerted on the body and the light source unit.

8. The probe as claimed in claim 7, wherein the elastic member is a spring having an inner diameter that is at least equal to a diameter of the through hole extending through the upper horizontal portion of the body.

9. The probe as claimed in claim 7, further comprising:
    a heat dissipating plate between the vertical portion of the structure and the light source unit.

10. The probe as claimed in claim 1, wherein the pressure application unit comprises:
    a structure having a weight sufficient to apply pressure to the object, and a horizontal portion and a vertical portion, wherein the vertical portion of the structure is connected in a perpendicular direction to the horizontal portion of the structure and has an end connected to the light source unit through a through hole in an upper horizontal portion of the body.

11. The probe as claimed in claim 10, further comprising:
a weight element placed on the horizontal portion of the structure to increase an amount of pressure applied to the object via the light source unit.

12. The probe as claimed in claim 11, further comprising:
a heat dissipating plate between the vertical portion of the structure and the light source unit.

13. The probe as claimed in claim 11, further comprising:
a heat dissipating plate between the vertical portion of the structure and the light source unit.

14. A biological signal measuring system, comprising:
a probe in which light is emitted onto a predetermined site of an object and the light transmitted through the object is detected;
a controller for controlling the operation of the probe and for recording and analyzing signals output from the probe;
a detected light intensity display unit for displaying an intensity of light detected by the probe; and
a biological signal display unit connected to the detected light intensity display unit for displaying a biological signal measured from an object,
wherein the probe includes:
a light source unit including a light source, the light source unit adapted to contact a predetermined site of the object and to emit light onto the predetermined site;
a photodetector unit positioned facing the light source unit for receiving the light emitted from the light source unit and transmitted through the object;
a body having a space for receiving the object and in which the light source unit and the photodetector unit are positioned along a same vertical axis with respect to a surface of the body supporting the object;
a pressure application unit coupled to the body for applying a pressure to the object via the light source unit, the pressure unit including a nut attached to an upper surface of the light source unit to be movable in a vertical direction and a bolt coupled to the nut; and
an elastic member between the nut and the light source unit,
wherein the pressure application unit is aligned in the same vertical axis above the light source unit; and
a pressure application break button electrically connected to the probe for allowing the subject or an operator to cease the application of pressure by the pressure application unit.

15. The biological signal measuring system as claimed in claim 14, further comprising:
a heat dissipating plate between the nut and the light source unit.

16. The biological signal measuring system as claimed in claim 14, further comprising:
a heat dissipating plate between the elastic member and the light source unit.

17. The biological signal measuring system as claimed in claim 14, wherein the pressure application unit comprises:
a structure having a horizontal portion and a vertical portion, wherein the horizontal portion contacts an upper surface of the body when the body is void of the object and protrudes above the upper surface of the body when the object is inserted into the body, and
wherein the vertical portion of the structure is connected in a perpendicular direction to the horizontal portion of the structure and has an end connected to the light source through a through hole in an upper horizontal portion of the body; and
an elastic member surrounding the vertical portion of the structure between the body and the light source unit such that an elastic force is exerted on the body and the light source unit.

18. The biological signal measuring system as claimed in claim 17, further comprising:
a heat dissipating plate between the vertical portion of the structure and the light source unit.

19. The biological signal measuring system as claimed in claim 14, wherein the pressure application unit comprises:
a structure having a weight sufficient to apply pressure to the object, and a horizontal portion and a vertical portion, wherein the vertical portion of the structure is connected in a perpendicular direction to the horizontal portion of the structure and has an end connected to the light source unit through a through hole in an upper horizontal portion of the body.

20. The biological signal measuring system as claimed in claim 19, further comprising:
a weight element placed on the horizontal portion of the structure to increase an amount of pressure applied to the object via the light source unit.

21. The biological signal measuring system as claimed in claim 20, further comprising:
a heat dissipating plate between the vertical portion of the structure and the light source unit.

22. The biological signal measuring system as claimed in claim 19, further comprising:
a heat dissipating plate between the vertical portion of the structure and the light source unit.

23. The biological signal measuring system as claimed in claim 14, wherein the biological signal display unit is a photoplethysmographic (PPG) display unit that displays a photoplethysmographic (PPG) wave from the object.

24. The biological signal measuring system as claimed in claim 23, further comprising:
a device selected from the group consisting of: an analog-to-digital converter (ADC), a programmable logic device (PLD), and a processor for recording a measured PPG wave.

25. The biological signal measuring system as claimed in claim 14, wherein the controller is a microprocessor.

* * * * *